US006284003B1

(12) United States Patent
Rose et al.

(10) Patent No.: US 6,284,003 B1
(45) Date of Patent: *Sep. 4, 2001

(54) OXIDATION COLORANTS COMPRISING 2-(2,5-DIAMINOPHENYL)-ETHANOL COMPOUNDS AND 2-CHLORO-6-METHYL-3-AMINOPHENOL COMPOUNDS

(75) Inventors: David Rose, Hilden; Horst Hoeffkes, Duesseldorf; Bernd Meinigke, Burscheid, all of (DE)

(73) Assignee: Henkel Kommanditgesellschaft auf Aktien, Duesseldorf (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,793
(22) PCT Filed: Nov. 8, 1995
(86) PCT No.: PCT/EP95/04385
§ 371 Date: May 19, 1997
§ 102(e) Date: May 19, 1997
(87) PCT Pub. No.: WO96/15765
PCT Pub. Date: May 30, 1996

(30) Foreign Application Priority Data

Nov. 17, 1994 (DE) .................................. 44 40 957

(51) Int. Cl.$^7$ ........................................... A61K 7/13
(52) U.S. Cl. ............................ 8/412; 8/407; 8/408; 8/410
(58) Field of Search .................. 8/406, 407, 408, 8/410, 412, 416, 421

(56) References Cited

U.S. PATENT DOCUMENTS

| 4,838,893 | 6/1989 | Rose et al. ................. 8/405 |
| 4,840,639 | 6/1989 | Husemeyer et al. ........... 8/410 |
| 4,865,774 | 9/1989 | Fabry et al. ............... 510/428 |
| 4,931,218 | 6/1990 | Schenker et al. ............ 510/498 |
| 5,021,066 | 6/1991 | Aeby et al. .................. 8/408 |
| 5,294,726 | 3/1994 | Behler et al. .............. 554/98 |

FOREIGN PATENT DOCUMENTS

| 28 31 847 | 2/1980 | (DE) . |
| 30 16 008 | 10/1981 | (DE) . |
| 36 27 398 | 2/1988 | (DE) . |
| 37 23 354 | 1/1989 | (DE) . |
| 37 25 030 | 2/1989 | (DE) . |
| 38 34 142 | 4/1990 | (DE) . |
| 39 26 344 | 2/1991 | (DE) . |
| 41 22 748 | 1/1993 | (DE) . |
| 0 007 537 | 2/1980 | (EP) . |
| 0 039 030 | 11/1981 | (EP) . |
| 0 063 736 | 11/1982 | (EP) . |
| 460128 * | 12/1991 | (EP) . |
| 2 168 727 | 6/1986 | (GB) . |
| 2239265 * | 12/1990 | (GB) . |
| WO 88/00823 | 2/1988 | (WO) . |

OTHER PUBLICATIONS

Cosmetics Science and Technology 2: 332–36 (1972).
Harry's Cosmeticology 547 (7th ed. 1982).
Ullmann's Encyclopedia of Industrial Chemistry A9: 100–103 (1987).
English language translation of EP 039,303, Henkel, pp. 1–13, Nov. 1981.*

* cited by examiner

Primary Examiner—Caroline D. Liott
(74) Attorney, Agent, or Firm—Wayne C. Jaeschke; Glenn E. J. Murphy; Kimberly R. Hild

(57) ABSTRACT

Oxidation dyes that contain a developer-coupler combination of 2-(2,5-diaminophenyl)-ethanol or its salt with an organic or inorganic acid and 2-chloro-6-methyl-3-aminophenol or its salt with an organic or inorganic acid are characterized by intensive blue finishes with high rubbing fastness.

9 Claims, No Drawings

OXIDATION COLORANTS COMPRISING 2-(2,5-DIAMINOPHENYL)-ETHANOL COMPOUNDS AND 2-CHLORO-6-METHYL-3-AMINOPHENOL COMPOUNDS

BACKGROUND OF THE INVENTION

This invention relates to oxidation colorants containing a special combination of primary and secondary intermediates for coloring keratin fibers.

By virtue of their intensive colors and good fastness properties, so-called oxidation colorants play a prominent role in the coloring of keratin fibers, particularly human hair. Oxidation colorants contain oxidation dye precursors, so-called primary intermediates and secondary intermediates. The primary intermediates form the actual dyes with one another or by coupling with one or more secondary intermediates in the presence of oxidizing agents or atmospheric oxygen.

Good oxidation dye precursors are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (levelling capacity). They must be resistant to light, heat and the effect of chemical reducing agents, for example permanent wave lotions. Finally, if they are used to color hair, they should not overly stain the scalp and, above all, should be toxicologically and dermatologically safe.

The primary intermediates normally used are primary aromatic amines containing another free or substituted hydroxy or amino group in the para position or the ortho position, diaminopyridine derivatives, heterocyclic hydrazones, 4-aminopyrazolone derivatives and 2,4,5,6-tetraaminopyrimidine and derivatives thereof.

Special representatives are, for example, p-toluylenediamine, 2,4,5,6-tetraaminopyrimidine, p-aminophenol, N,N-bis-(2-hydroxyethyl)-p-phenylenediamine, 2-(2,5-diaminophenyl)-ethanol, 2-(2,5-diaminophenoxy)-ethanol, 1-phenyl-3-carboxyamido-4-amino-5-pyrazolone and 4-amino-3-methylphenol, 2-hydroxy4,5,6-triaminopyrimidine, 2,4-dihydroxy-5,6-diaminopyrimidine and 2,5,6-triaminohydroxypyrimidine.

The secondary intermediates used are generally m-phenylenediamine derivatives, naphthols, resorcinol and resorcinol derivatives, pyrazolones and m-aminophenols. Particularly suitable secondary intermediates are α-naphthol, pyrogallol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-amino-phenol, 1,3-bis-(2,4-diaminophenoxy)-propane, 2-chlororesorcinol, 2-chloro-6-methyl-3-aminophenol and 2-methyl resorcinol By combination with various secondary intermediates, a certain primary intermediate can form a broad range of color tones. Nevertheless, it is often not possible to obtain the large range of natural color tones with a single primary intermediate. In practice, therefore, a combination of various primary intermediates and secondary intermediates has to be used to obtain a single natural-looking color. Accordingly, there is a constant need for new improved secondary intermediate/primary intermediate combinations. This applies in particular to the blues where conventional dyes are often not entirely satisfactory in their level-dyeing capacity and their resistance to cold waving and washing.

Accordingly, the problem addressed by the present invention was to provide new primary intermediate/secondary intermediate combinations in the blue range which would satisfy the requirements oxidation dye precursors are expected to meet to a particular degree.

It has now surprisingly been found that a special combination of a known secondary intermediate and a known primary intermediate leads to dark blue colors of high brilliance which are additionally distinguished by high fastness to rubbing.

DESCRIPTION OF THE INVENTION

The present invention relates to oxidation colorants for coloring keratin fibers containing secondary intermediates and primary intermediates in a water-containing carrier, characterized in that 2-(2,5-diaminophenyl)-ethanol or a salt thereof with an inorganic or organic acid is present as the primary intermediate while 2-chloro-6-methyl-3-aminophenol or a salt thereof with an inorganic or organic acid is present as the secondary intermediate.

In the context of the invention, keratin fibers are understood to include pelts, wool, feathers and, in particular, human hair. Although the oxidation colorants according to the invention are particularly suitable for coloring keratin fibers, there are no basic obstacles to their use in other fields, particularly in color photography.

The primary intermediate according to the invention is already known from DE-OS 28 31 847 to which reference is expressly made regarding the production of this compound.

The secondary intermediate according to the invention is known from DE-OS 30 16 008 as a secondary intermediate for intensive blue tones in particular. Accordingly, reference is expressly made to this document also.

However, there is no reference in either of these documents to the combination according to the invention or even to its highly advantageous properties.

The primary and secondary intermediates according to the invention may be used both as free bases and in the form of their inorganic or organic salts, for example hydrochlorides or hydrobromides.

The hair colorants according to the invention contain both the primary intermediates and the secondary intermediates in a quantity of preferably 0.01 to 20% by weight and, more preferably 0.5 to 5% by weight, based on the oxidation colorant as a whole. The primary intermediates and secondary intermediates are generally used in substantially equimolar quantities. Although the equimolar amounts of primary and secondary intermediates have proven expedient, a certain excess of individual oxidation dye precursors is not a disadvantage, so that the primary intermediates and secondary intermediates may be present in a molar ratio of 1:0.5 to 1:2.

In addition to the primary intermediate/secondary intermediate combination according to the invention, the hair colorants may optionally contain other primary intermediates and/or secondary intermediates to obtain special color tones. Suitable compounds were mentioned in the acknowledgement of the prior art.

In one preferred embodiment, the hair colorants according to the invention contain typical substantive dyes in addition to the oxidation dye precursors in quantities of 0.01 to 20% by weight, based on the oxidation hair colorant as a whole, for further modifying the color tones. The typical substantive dyes in question may be selected, for example, from the group of nitrophenylenediamines, nitroaminophenols, anthraquinones or indophenols, for example the compounds known under the international names or trade names of HC Yellow 2, HC Yellow 4, Basic Yellow 57, Disperse Orange 3, HC Red 3, HC Red BN, Basic Red 76, HC Blue 2, Nitroblau, Disperse Blue 3, Basic Blue 99, HC Violet 1, Disperse Violet 1, Disperse Violet 4, Disperse Black 9, Basic Brown 16, picramic acid and Rodol 9 R.

The oxidation dye precursors and the substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

To produce the colorants according to the invention, the oxidation dye precursors are incorporated in a suitable water-containing carrier. For coloring hair, such carriers are, for example, cremes, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and also hydroxyl groups may also be present in the molecule. The following are examples of suitable anionic surfactants—in the form of the sodium, potassium and ammonium salts and the mono-, di- and trialkanol-ammonium salts containing 2 or 3 carbon atoms in the alkanol group:

linear fatty acids containing 10 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups, linear alkane sulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—OSO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule, sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and C$_{12-18}$ acyl sarcosine.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group, C$_{12-22}$ fatty acid monoesters and diesters of products of the addition of 1 to 30 moles of ethylene oxide to glycerol, C$_{8-22}$ alkyl mono- and oligoglycosides and ethoxylated analogs thereof, products of the addition of 5 to 60 moles of ethylene oxide to castor oil and hydrogenated castor oil, products of the addition of ethylene oxide to sorbitan fatty acid esters, products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil® -Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the dialkyl ammonium methosulfates and methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkyl metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/ vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, dyes for coloring the formulations, anti-dandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV absorbers, consistency promoters, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

Basically, the color may be oxidatively developed with atmospheric oxygen. However, a chemical oxidizing agent is preferably used, particularly when human hair is to be not only colored, but also lightened. Particularly suitable oxidizing agents are hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. One example of an enzymatic process is the procedure whereby the effect of small quantities (for example 1% and less, based on the formulation as a whole) of hydrogen peroxide is enhanced by peroxidases.

The preparation of the oxidizing agent is best mixed with the preparation of the oxidation dye precursors immediately before coloring of the hair. The ready-to-use hair coloring preparation formed should preferably have a pH value of 6 to 10. In a particularly preferred embodiment, the hair colorant is used in a mildly alkaline medium. The application temperatures may be in the range from 15 to 40° C. After a contact time of about 30 minutes, the hair colorant is removed from the hair to be colored by rinsing. There is no need for the hair to be washed with a shampoo where a carrier of high surfactant content, for example a coloring shampoo, has been used.

The following Example is intended to illustrate the invention.

EXAMPLE

A cream base of the following composition was initially prepared:

| | |
|---|---|
| Tallow fatty alcohol | 17.0 |
| Lorol ® techn.[1] | 4.0 |
| Texapon ® N 28[2] | 40.0 |
| Dehyton ® K[3] | 25.0 |
| Eumulgin ® B 2[4] | 1.5 |
| Distilled water | 12.5 |

[1] $C_{12-18}$ fatty alcohol (HENKEL)

[2] Sodium lauryl ether sulfate (ca. 28% active substance; CTFA name: Sodium Laureth Sulfate) (HENKEL)

[3] Fatty acid amide derivative of betaine structure with the formula $R-CONH(CH_2)_3N^+(CH_3)_2CH_2COO^-$ (ca. 30% active substance; CTFA name Cocoamidopropyl Betaine) (HENKEL)

[4] Cetostearyl alcohol containing around 20 moles of EO (CTFA name: Ceteareth-20) (HENKEL)

On the basis of this cream, the following hair coloring cream emulsion was then prepared:

| | | |
|---|---|---|
| Cream base | 50.0 | |
| Primary intermediate | 7.5 | mmoles |
| Secondary intermediate | 7.5 | mmoles |
| $Na_2SO_3$ (inhibitor) | 1.0 | |
| $(NH_4)_2SO_4$ | 1.0 | |
| Conc. ammonia solution | to pH 10 | |
| Water | to 100 | |

The components were mixed with one another in the above order. After addition of the oxidation dye precursors and the inhibitor, the pH value of the emulsion was initially adjusted to 10 with concentrated ammonia solution, after which the emulsion was made up with water to 100 g.

The color was oxidatively developed with 3% hydrogen peroxide solution as oxidation solution. To this end, 50 g of hydrogen peroxide solution (3%) were added to and mixed with 100 g of the emulsion.

The coloring cream was applied to approximately 5 cm long tresses of standardized, 90% grey, but not specially pretreated human hair and left thereon for 30 minutes at 32° C. After the coloring process, the hair was rinsed, washed with a standard shampoo and then dried.

The color obtained with the primary intermediate/secondary intermediate combination according to the invention was dark blue. The fastness of the colored hair to rubbing was very high.

In addition, the colors obtained with the following hair coloring cream emulsions based on the above-mentioned formulation were investigated:

| | B1 | B2 | B3 |
|---|---|---|---|
| Primary intermediate: 2-(2,5-Diaminophenyl)-ethanol | 7.5 mmoles | 7.5 mmoles | 7.5 mmoles |
| Secondary intermediate: 2-Chloro-6-methyl-3-aminophenol | 7.5 mmoles | 7.5 mmoles | 7.5 mmoles |
| Other components: | | | |
| 5-Amino-2-methyl phenol | 0.025 | — | 0.05 |
| 4-(N-2-Hydroxyethyl)-3-nitro-aniline | 0.25 | — | — |
| 2-Amino-6-chloro-4-nitro-phenol | — | 0.25 | — |
| Resorcinol | — | 0.17 | — |
| 2,4,5,6-Tetraaminopyrimidine | — | — | 0.13 |
| Color | Magenta | Intensive brown | Violet |

What is claimed is:

1. An oxidation colorant for coloring keratin fibers, comprising a primary intermediate selected from the group consisting of 2-(2,5-diaminophenyl)-ethanol and organic or inorganic acid salts thereof, a secondary intermediate selected from the group consisting of 2-chloro-6-methyl-3-aminophenol and organic or inorganic acid salts thereof, and a water-containing carrier.

2. An oxidation colorant according to claim 1, wherein the primary intermediate comprises 0.01% to 20% by weight and the secondary intermediate comprises 0.01% to 20% by weight, said weight percents based on the weight of the oxidation colorant as a whole.

3. An oxidation colorant according to claim 2, wherein the primary intermediate comprises 0.5% to 5% by weight and the secondary intermediate comprises 0.5% to 5% by weight, said weight percents based on the weight of the oxidation colorant as a whole.

4. An oxidation colorant according to claim 3, further comprising at least one other primary intermediate or at least one other secondary intermediate.

5. An oxidation colorant as claimed in claim 4, further comprising a substantive dye.

6. An oxidation colorant as claimed in claim 5, further comprising a surfactant.

7. An oxidation colorant according to claim 3, wherein the primary intermediate is 2-(2,5-diaminophenyl)-ethanol and the secondary intermediate is 2-chloro-6-methyl-3-aminophenol.

8. A method of coloring keratin fibers, comprising preparing an oxidation colorant according to claim 1, contacting said oxidation colorant with an oxidizing agent selected from the group consisting of atmospheric oxygen, peroxides, and peroxidases, and applying said oxidation colorant contacted with said oxidizing agent to a fiber to effect coloration thereof.

9. A method according to claim 8, wherein the primary intermediate is 2-(2,5-diaminophenyl)-ethanol, the secondary intermediate is 2-chloro-6-methyl-3-aminophenol, and the oxidizing agent is hydrogen peroxide or an addition product thereof with urea, melamine, or sodium borate.

\* \* \* \* \*